United States Patent [19]

Renga et al.

[11] 4,331,604

[45] May 25, 1982

[54] PREPARATION OF CYCLIC CARBONATES

[75] Inventors: James M. Renga; Roy A. Periana-Pillai, both of Midland, Mich.

[73] Assignee: The Dow Chemical Company, Midland, Mich.

[21] Appl. No.: 284,036

[22] Filed: Jul. 17, 1981

[51] Int. Cl.³ .................. C07D 317/36; C07D 317/38; C07D 317/44; C07D 317/46
[52] U.S. Cl. ..................................... 549/230; 549/229
[58] Field of Search ...................................... 260/340.2

[56] References Cited

PUBLICATIONS

Pews, J. A. Chem. Soc. Chem. Comm., 1974, 119.

*Primary Examiner*—Norma S. Milestone
*Attorney, Agent, or Firm*—Douglas N. Deline

[57] ABSTRACT

The thermal decomposition of a β-halogenated aliphatic carbonate at about 100° C.–300° C. to produce a cyclic alkylene carbonate and an aliphatic halide is accelerated by the presence of a polar solvent, preferably the cyclic carbonate product. Further improvement may be obtained when there is additionally present a mercury compound.

12 Claims, No Drawings

PREPARATION OF CYCLIC CARBONATES

BACKGROUND OF THE INVENTION

This invention relates to a new catalytic chemical process for making cyclic alkylene carbonates.

Cyclic carbonates such as ethylene carbonate and propylene carbonate are useful solvents and chemical intermediates. Commonly used processes for making these cyclic esters include the reaction of phosgene with the appropriate glycol and the reaction of a chlorohydrin with carbon dioxide, both carried out in the presence of a base and thus involving the production of a large amount of salt as an undesirable waste by-product.

It is known that β-brominated alkyl carbonates such as 2,3-dibromopropyl ethyl carbonate and 2-bromoethyl ethyl carbonate undergo pyrolysis on long heating at about 200° C. to produce bromomethylethylene carbonate and ethylene carbonate, respectively, with ethyl bromide as a co-product in each case, see Pews, J.C.S. Chem. Comm., 1974, p. 119. It is also known that these brominated alkyl carbonates and their chlorinated analogs were converted to corresponding alkylene epoxides when they are heated in the presence of a quaternary ammonium or phosphonium salt. This reaction is described in applications of one of us and another, see Renga and Emmons, Ser. No. 095,002, filed Nov. 16, 1979, now U.S. Pat. No. 4,261,906, also Ser. No. 238,188, filed Feb. 25, 1981, entitled "Process for Making Vicinal Epoxides and Dihalides", same inventors.

SUMMARY OF THE INVENTION

It has now been found that the decomposition of a β-halogenated alkyl carbonate to form a cyclic alkylene carbonate and an alkyl halide is greatly facilitated and accelerated by the presence of at least about 20 mole percent of a polar solvent selected from the group consisting of a cyclic alkylene carbonate and other highly polar solvents such as N,N-dimethylformamide, N,N-dimethylacetamide, sulfolane, pyrrolidinone, and the like. This reaction which takes place at about 100° C.–300° C., is undergone by halogenated alkyl carbonate esters having the formula

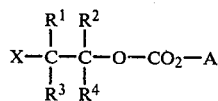

wherein A is an alkyl group, preferably a lower alkyl group, or a group of the formula

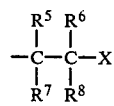

wherein each R group individually is hydrogen, a hydrocarbon group, —CH$_2$X, —CH$_2$Y, and each of the pairs R$^1$, R$^2$ and R$^5$, R$^6$ may together form an alkylene group of 3–6 carbon atoms, each X is individually Cl, Br, or I, and Y is an alkoxy or aroxy group. The products of the reaction are a halide AX and an alkylene carbonate of the formula

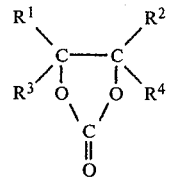

DETAILED DESCRIPTION OF THE INVENTION

In the present reaction, the preferred temperature is about 150° C.–250° C. to provide an optimum combination of conversion and yield with a practical reaction time of about 0.1–10 hours, depending upon the particular halogenated carbonate starting material and especially the halogen in that carbonate ester. Although brominated and iodinated carbonate esters offer faster reaction rates at a given temperature, the chlorinated esters are preferred starting materials in most cases, primarily for economic reasons.

Effective promotion of the decomposition reaction is accomplished by mixing at least about 20 mole percent and preferably about 20–200 percent of the polar solvent with the stirring β-halogenated carbonate and heating the resulting mixture to the specified temperature, preferably to about 150° C.–250° C. In some cases, the preferred polar solvent is the cyclic alkylene carbonate product of the reaction. More than one polar solvent may be employed. For convenience in operating, the polar solvent additive has a boiling point at atmospheric pressure within the process range, i.e., at least about 100° C., preferably at least 150° C.

In many instances, optimum results are obtained when both a polar solvent and a chemically combined mercury catalyst as described in our concurrently filed companion application Ser. No. 284,037 are combined with the β-halogenated carbonate in the reaction mixture. Such mercury catalysts comprise essentially any mercuric or mercurous compound. Mercuric salts which are somewhat more soluble in the starting halogenated carbonate are preferred, for example, mercuric chloride, mercuric acetate, mercuric bromide, and mercuric sulfate. The proportion of mercury compound is not critical as any significant amount of mercury has a catalytic effect. In practice, about 0.05–10 mole percent of mercury based on the halogenated alkyl carbonate is a convenient proportion and a preferred range of mercury concentration is about 1–5 mole percent.

In the above formulas, the term "hydrocarbon group" includes alkyl groups of one to about 20 carbon atoms, cycloalkyl and alkylcycloalkyl groups of 5–10 carbon atoms, and aromatic hydrocarbon groups of 6–10 carbon atoms. Thus, groups such as methyl, ethyl, isopropyl, hexyl, dodecyl, and octadecyl are encompassed by the definition, also groups such as cyclopentyl, cyclohexyl, dimethylcyclohexyl, phenyl, tolyl, and xylyl are included.

The symbol Y defines alkoxy groups, preferably alkoxy groups of 1–4 carbon atoms such as methoxy, ethoxy, isopropoxy, t-butoxy, and the like, and also aroxy groups such as a phenol or bisphenol residue.

In a preferred mode of the present process, the symbol A in the above halogenated carbonate formula represents an alkyl group, most preferably a lower alkyl group such as methyl, ethyl, isopropyl, or butyl. Carbonates where A is methyl or ethyl are advantageous in that the methyl or ethyl halide co-product is most readily vaporized from the reaction mixture, thereby driving the reaction to rapid completion and also facilitating the separation of the relatively high boiling cyclic carbonate product from the residual reaction mixture as a pure material.

When A represents the halogenated group of the formula

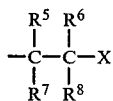

The process is somewhat complicated by the fact that two cyclic carbonates and two alkylene halides are produced, these products having the formulas

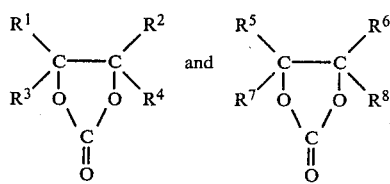

plus

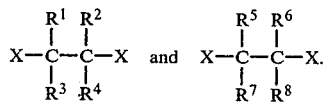

In these cases it is advantageous to apply a partial vacuum to the RXN system to facilitate the removal of the alkylene halides. In the case where an unsymmetrical carbonate ester is the starting material and the groups $R^{1-4}$ differ in at least one instance from the groups $R^{5-8}$, the two different cyclic carbonates and the two different alkylene dihalides are ordinarily readily separable by conventional means and, of course, all of the reaction products are commercially valuable compounds as is the case in the mode discussed previously where A represents an alkyl group. Additionally, when an unsymmetrical halogenated carbonate starting material of the above type is employed, the cyclic carbonate product having the higher carbon content is favored. Thus, when $R^{1-4}$ together contain more carbon atoms than $R^{5-8}$, the products

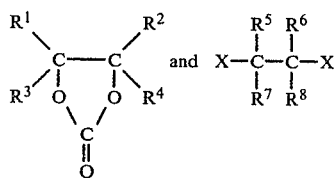

are the major carbonate and dihalide products. Also, a difference in the halogen atoms in the halogenated carbonate starting material affects the course of the reaction. For example, when one X is Cl and the other X is Br in a di(haloalkyl) carbonate, the more labile Br atom favors the formation of the cyclic carbonate derived from the bromoalkyl group.

Obviously, when a symmetrical bis(haloalkyl) carbonate is employed and

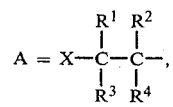

only one cyclic carbonate and one alkylene dihalide are produced.

The β-halogenated alkyl carbonate starting materials for this process can be prepared by several known procedures. The reaction of a chloroformate with an alcohol in the presence of an acid receptor such as pyridine conventionally used for the preparation of carbonate esters is readily adapted to the preparation of these halogenated carbonates by using the appropriate halogenated alcohol and halogenated alkyl chloroformate reactants. Symmetrical bis(haloalkyl) carbonates in particular can be made by the strong acid catalyzed transesterification reaction of a halogenated alcohol in excess with a dialkyl carbonate. Some of these carbonates can also be made by using an appropriate unsaturated alcohol in the transesterification reaction and then adding halogen or hydrogen halide to the unsaturated ester product. Pechukas, U.S. Pat. No. 2,518,058, describes a method for making β-haloalkyl alkyl carbonates by the reaction of an epoxide with a haloformate.

The present process is conveniently operated merely by combining the β-halogenated alkyl carbonate ester and the polar solvent or solvents, optionally plus a mercury compound catalyst as previously defined, and heating the mixture, whereupon the relatively volatile alkyl halide or alkylene dihalide co-product distills from the reaction mixture and can be recovered by condensing it or by other appropriate means. The cyclic carbonate product is ordinarily distilled from the residual reaction mixture, usually under reduced pressure.

An inert reaction solvent or diluent is not required and the process is readily operated in the absence of such an additive. Inert solvents suitable for use include hydrocarbons such as toluene, xylene, and decane, also glycol diethers such as dimethoxyethane and the diethyl diether of diethylene glycol.

EXAMPLE 1

Allyl methyl carbonate was prepared by the transesterification reaction of allyl alcohol with dimethyl carbonate in the presence of sodium methoxide. The allyl methyl carbonate product was separated by distillation of the reaction mixture and it was reacted with an equivalent of chlorine to produce 2,3-dichloropropyl methyl carbonate.

Using a 25 ml reaction flask equipped with a condenser connected to a receiver containing 10 ml of methylene chloride and cooled by a mixture of solid carbon dioxide and acetone, a mixture of 5.6 g (0.03 g mole) of 2,3-dichloropropyl methyl carbonate and 1.77 g (0.013 g mole) of 4-(chloromethyl)-1,3-dioxol-2-one (chloromethylethylene carbonate) was heated for one hour at 250° C. At this point, gas chromatographic and nuclear magnetic resonance (NMR) spectroscopic analyses of both the residual mixture in the reaction flask and the condensate in the receiver indicated that all of the starting 2,3-dichloropropyl methyl carbonate had been reacted with a 91 percent selectivity to the cyclic carbonate, 4-chloromethyl-1,3-dioxol-2-one. When the 2,3-dichloropropyl methyl carbonate was heated at the same temperature with no initially added cyclic carbonate product, four hours of heating were required to obtain essentially the same results.

EXAMPLE 2

The procedure of Example 1 was repeated except for substituting an equal molar proportion of tetramethylene sulfone for the added cyclic carbonate in the initial reaction mixture. In 1.25 hours of heating this mixture at 250° C., all of the 2,3-dichloropropyl methyl carbonate had been converted with an 87 percent selectivity to the cyclic carbonate, 4-(chloromethyl)-1,3-dioxol-2-one.

EXAMPLE 3

The procedure of Example 1 was repeated except that the reaction mixture was an equimolar mixture of 2,3-dichloropropyl methyl carbonate and 4-(chloromethyl)-1,3-dioxol-2-one. The progress of the reaction was followed to complete conversion of the 2,3-dichloropropyl methyl carbonate by periodic gas chromatographic analyses of the reaction mixture. The progress of a similar reaction starting with pure 2,3-dichloro-1-propyl methyl carbonate was followed in the same way for comparison. These results are listed in Table I.

TABLE I

| Time | % Conversion | |
| min. | 50% Diluent | No Diluent |
| --- | --- | --- |
| 0 | 50 | 0 |
| 15 | 80 | — |
| 30 | 90 | — |
| 45 | 97 | — |
| 60 | 100 | ~7 |
| 120 | | 25 |
| 150 | | 50 |
| 180 | | 90 |
| 210 | | 100 |

It is evident that there was a long induction period before appreciable conversion of the undiluted carbonate took place. In each case, the selectivity of the reaction was about 90 percent to the cyclic carbonate, 4-(chloromethyl)-1,3-dioxol-2-one.

EXAMPLE 4

A mixture of 5.76 g (0.02 g mole) of trans-2-bromo-1-cyclohexyl 2-chloroethyl carbonate and 1.76 g (0.02 g mole) of ethylene carbonate was heated at 170° C. for 13 hours. Distillation of the reaction mixture gave 2.53 g (89 percent yield) of cis-1,2-carbonyldioxycyclohexane (1,2-cyclohexylene carbonate) b.p. 95° C.–100° C./0.4 mm Hg.

EXAMPLES 5–8

A series of experiments was carried out essentially as described in Example 1 wherein 0.01 g mole portions of 2,3-dichloro-1-propyl methyl carbonate were heated at 220°–225° C. as the pure compound, combined with different amounts of the cyclic carbonate product, combined with a mixture of the cyclic carbonate product and mercuric acetate, and with mercuric acetate alone. The heating was continued to 100 percent conversion in each case except for the pure compound control where little conversion had taken place after one hour. The selectivity of the reaction to the cyclic carbonate was estimated by analysis of the reaction mixture as before. The results are listed in Table II.

TABLE II

| Example No. | g mole catalyst | | Time min. | Conv. % | Sel. % |
| | cyclic carbonate | Hg (OAc)$_2$ | | | |
| --- | --- | --- | --- | --- | --- |
| Control | — | — | 60 | ~7 | — |
| 5 | 0.01 | — | 75 | 100 | 85 |
| 6 | 0.02 | — | 30 | 100 | 87 |
| 7 | 0.01 | 0.0002 | 30 | 100 | 92 |
| 8 | — | 0.0002 | 60 | 100 | 95 |

In the same way as shown in the above examples using a polar additive or a combination thereof with a mercury catalyst, other cyclic carbonates are prepared by decomposition of the appropriate β-halogenated alkyl carbonates. For example, 4-(methoxymethyl)-1,3-dioxol-2-one (methoxymethylethylene carbonate) is produced from 1-chloro-3-methoxy-2-propyl methyl carbonate, 4-(hexyloxymethyl)-1,3-dioxol-2-one is made from 1-chloro-3-hexyloxy-2-propyl ethyl carbonate, and 4-(phenoxymethyl)-1,3-dioxol-2-one is made from bis(1-chloro-3-phenoxy-2-propyl) carbonate. Also, by this process ethylene carbonate is made from 2-chloroethyl methyl carbonate, propylene carbonate is made from 1-chloro-2-propyl ethyl carbonate, and 1,2-octylene carbonate is made from 1-chloro-2-octyl methyl carbonate.

EXAMPLE 9

A mixture of 4.9 g (0.02 mole) of 2-bromoethyl 1-chloro-2-propyl carbonate and 2.04 g (0.02 mole) of propylene carbonate was heated at 170° C. in a 25 ml flask equipped with a dry ice cooled receiver. The mixture was heated for 3 hours under a partial vacuum of 100 mm Hg. Distillation of the reaction mixture gave 1.33 g (76 percent yield) of ethylene carbonate.

We claim:

1. A process for making a cyclic carbonate of the formula

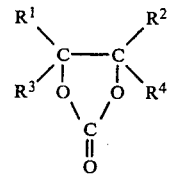

which comprises mixing a β-halogenated carbonate ester with at least about 20 mole percent of an inert polar solvent and heating the resulting mixture at about 100° C.–300° C., said β-halogenated carbonate ester having the formula

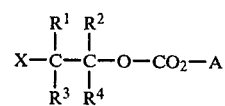

wherein A represents an alkyl group or a group of the formula

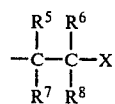

wherein the R groups are individually hydrogen, a hydrocarbon group, —$CH_2X$, —$CH_2Y$, and each of the pairs $R^1$, $R^2$ and $R^5$, $R^6$ may together form an alkylene group of 3–6 carbon atoms, each X is individually Cl, Br, or I, and Y is an alkoxy or aroxy group.

2. The process of claim 1 wherein the polar solvent selected from the group consisting of a cyclic alkylene carbonate, N,N-dimethylformamide, N,N-dimethylacetamide, sulfolane, and 2-pyrrolidinone.

3. The process of claim 1 wherein the polar solvent has an atmospheric boiling point of at least about 150° C.

4. The process of claim 3 wherein the polar solvent is a cyclic alkylene carbonate.

5. The process of claim 4 wherein the cyclic carbonate is the cyclic carbonate product of the process.

6. The process of claim 1 wherein the temperature is about 150° C.–250° C.

7. The process of claim 1 wherein X represents Cl.

8. The process of claim 1 wherein A represents a lower alkyl group.

9. The process of claim 8 wherein the β-halogenated carbonate is 2,3-dichloropropyl methyl carbonate and the cyclic alkylene carbonate product is chloromethylethylene carbonate.

10. The process of claim 1 wherein A represents a β-haloalkyl group.

11. The process of claim 10 wherein the β-halogenated carbonate is trans 2-bromo-1-cyclohexyl 2-chloroethyl carbonate and the cyclic alkylene carbonate product is cis 1,2-carbonyldioxycyclohexane.

12. The process of claim 1 wherein the β-halogenated carbonate ester-polar solvent mixture also includes a catalytically effective amount of chemically combined mercury.

* * * * *

UNITED STATES PATENT AND TRADEMARK OFFICE
CERTIFICATE OF CORRECTION

PATENT NO. : 4,331,604
DATED : May 25, 1982
INVENTOR(S) : James M. Renga and Roy A. Periana-Pillai It is certified that error appears in the above—identified patent and that said Letters Patent is hereby corrected as shown below:

Column 1, line 25, "logs were converted" should read -- logs are converted --.

Column 2, line 26, "with the stirring" should read -- with the starting --.

Column 3, line 16, "The process is" should read -- the process is --.

Signed and Sealed this

Fifteenth Day of February 1983

[SEAL]

Attest:

Attesting Officer

GERALD J. MOSSINGHOFF
Commissioner of Patents and Trademarks